US009173677B2

(12) United States Patent
Marczyk et al.

(10) Patent No.: US 9,173,677 B2
(45) Date of Patent: Nov. 3, 2015

(54) APPARATUS AND METHOD FOR TRANSVAGINAL SURGERY

(75) Inventors: Stanislaw Marczyk, Stratford, CT (US); Russell Pribanic, New Milford, CT (US); Kevin Sniffin, Danbury, CT (US)

(73) Assignee: Covidien LP, Mansfield, MA (US)

( * ) Notice: Subject to any disclaimer, the term of this patent is extended or adjusted under 35 U.S.C. 154(b) by 282 days.

(21) Appl. No.: 12/830,762

(22) Filed: Jul. 6, 2010

(65) Prior Publication Data

US 2011/0009704 A1    Jan. 13, 2011

Related U.S. Application Data

(60) Provisional application No. 61/223,853, filed on Jul. 8, 2009.

(51) Int. Cl.
*A61B 1/32*    (2006.01)
*A61B 17/34*   (2006.01)
*A61B 17/00*   (2006.01)

(52) U.S. Cl.
CPC ......... *A61B 17/3423* (2013.01); *A61B 17/3431* (2013.01); *A61B 2017/00278* (2013.01);
(Continued)

(58) Field of Classification Search
CPC ................ A61B 2017/00557; A61B 17/0218; A61B 17/3462; A61B 17/3415; A61B 17/3417; A61B 17/3421; A61B 17/3423; A61B 2017/3419; A61B 2017/3425; A61B 2017/344; A61B 2017/22072; A61B 2017/3454

USPC ......... 606/119, 108, 213, 135, 191–193, 197; 600/1–8, 29–32, 35, 38–40; 604/218, 604/906

See application file for complete search history.

(56) References Cited

U.S. PATENT DOCUMENTS 2,849,002 A  *  8/1958  Oddo ............................ 606/192
4,782,834 A  * 11/1988  Maguire et al. ............... 606/194
(Continued)

FOREIGN PATENT DOCUMENTS

EP    0950376 A1    10/1990
EP    1 774 918 A1    4/2007
(Continued)

OTHER PUBLICATIONS

European Search Report for corresponding EP10251218 date of mailing is Jul. 6, 2011 (4 pages).

*Primary Examiner* — Anu Ramana
*Assistant Examiner* — Jessica Weiss

(57) ABSTRACT

An access port for performing surgery transvaginally is provided. The access port includes an elongated flexible member having proximal and distal ends and a central portion therebetween, and a retention mechanism formed on the distal end of the elongated member. The retention mechanism includes a first configuration for inserting the distal end of the elongated member within an opening and a second configuration for selectively securing the elongated member within an opening. Also provided is a method of performing a transvaginal surgery. The method includes providing an access port including a retention mechanism configured to selectively retain the access port within the vagina of a patient, forming an incision in the wall of the vagina into the abdomen of the patient, inserting a distal end of the access port into the vagina and through the incision, and activating the retention mechanism to secure the distal end of the access port within the abdominal cavity of the patient.

14 Claims, 16 Drawing Sheets

(52) U.S. Cl.
CPC ... *A61B2017/346* (2013.01); *A61B 2017/3445* (2013.01); *A61B 2017/3454* (2013.01); *A61B 2017/3486* (2013.01); *A61B 2017/3488* (2013.01)

(56) References Cited

U.S. PATENT DOCUMENTS

| | | | |
|---|---|---|---|
| 5,002,557 A | 3/1991 | Hasson | |
| 5,122,122 A | 6/1992 | Allgood | |
| 5,176,697 A | 1/1993 | Hasson et al. | |
| 5,209,754 A | 5/1993 | Ahluwalia | |
| 5,217,466 A | 6/1993 | Hasson | |
| 5,290,249 A | 3/1994 | Foster et al. | |
| 5,312,391 A | 5/1994 | Wilk | |
| 5,336,203 A | 8/1994 | Goldhardt et al. | |
| 5,345,927 A | 9/1994 | Bonutti | |
| 5,375,588 A | 12/1994 | Yoon | |
| 5,394,863 A | 3/1995 | Sanford et al. | |
| 5,445,615 A | 8/1995 | Yoon | |
| 5,464,409 A | 11/1995 | Mohajer | |
| 5,514,091 A * | 5/1996 | Yoon | 604/103.11 |
| 5,514,133 A | 5/1996 | Golub et al. | |
| 5,520,698 A | 5/1996 | Koh | |
| 5,556,385 A | 9/1996 | Andersen | |
| 5,624,399 A | 4/1997 | Ackerman | |
| 5,643,285 A | 7/1997 | Rowden et al. | |
| 5,656,013 A | 8/1997 | Yoon | |
| 5,697,946 A | 12/1997 | Hopper et al. | |
| 5,836,913 A | 11/1998 | Orth et al. | |
| 5,840,077 A | 11/1998 | Rowden et al. | |
| 5,842,971 A | 12/1998 | Yoon | |
| 6,099,506 A | 8/2000 | Macoviak et al. | |
| 6,156,006 A | 12/2000 | Brosens et al. | |
| 6,183,520 B1 * | 2/2001 | Pintauro et al. | 623/23.64 |
| 6,228,063 B1 | 5/2001 | Aboul-Hosn | |
| 6,293,952 B1 | 9/2001 | Brosens et al. | |
| 6,328,720 B1 | 12/2001 | McNally et al. | |
| 6,454,783 B1 | 9/2002 | Piskun | |
| 6,485,410 B1 * | 11/2002 | Loy | 600/135 |
| 6,524,283 B1 | 2/2003 | Hopper et al. | |
| 6,572,631 B1 | 6/2003 | McCartney | |
| 6,676,639 B1 | 1/2004 | Ternström | |
| 6,706,050 B1 | 3/2004 | Giannadakis | |
| 6,997,909 B2 | 2/2006 | Goldberg | |
| 7,100,614 B2 | 9/2006 | Stevens et al. | |
| 7,160,309 B2 | 1/2007 | Voss | |
| 7,235,064 B2 | 6/2007 | Hopper et al. | |
| 7,625,361 B2 | 12/2009 | Suzuki et al. | |
| 7,721,742 B2 | 5/2010 | Kalloo et al. | |
| 7,798,898 B2 | 9/2010 | Luciano, Jr. et al. | |
| 2004/0111061 A1 | 6/2004 | Curran | |
| 2004/0193181 A1 * | 9/2004 | Bonutti | 606/119 |
| 2005/0096695 A1 | 5/2005 | Olich | |
| 2005/0216028 A1 * | 9/2005 | Hart et al. | 606/108 |
| 2006/0129165 A1 | 6/2006 | Edoga et al. | |
| 2006/0247499 A1 | 11/2006 | Butler et al. | |
| 2007/0203517 A1 * | 8/2007 | Williams et al. | 606/191 |
| 2007/0225744 A1 * | 9/2007 | Nobles et al. | 606/192 |
| 2008/0119868 A1 | 5/2008 | Sharp et al. | |
| 2008/0255519 A1 | 10/2008 | Piskun et al. | |
| 2008/0262300 A1 * | 10/2008 | Ewers et al. | 600/114 |
| 2009/0204067 A1 | 8/2009 | Abu-Halawa | |
| 2009/0326332 A1 | 12/2009 | Carter | |
| 2010/0063452 A1 | 3/2010 | Edelman et al. | |

FOREIGN PATENT DOCUMENTS

| | | |
|---|---|---|
| EP | 2044889 A1 | 4/2009 |
| WO | WO 97/33520 | 9/1997 |
| WO | WO99/16368 A1 | 4/1999 |
| WO | WO 01/49363 A1 | 7/2001 |
| WO | WO2008/042005 A1 | 4/2008 |
| WO | WO 2008/093313 A1 | 8/2008 |

* cited by examiner

APPARATUS AND METHOD FOR TRANSVAGINAL SURGERY

CROSS-REFERENCE TO RELATED APPLICATION

The present application claims the benefit of, and priority to, U.S. Provisional Patent Application Ser. No. 61/223,853, filed Jul. 8, 2009, the disclosure of which is disclosed herein by reference in its entirety.

BACKGROUND

1. Technical Field

The present disclosure relates to transvaginal surgery. More particularly, the present disclosure relates to an apparatus and method for use in transvaginal surgery for accessing the abdominal cavity.

2. Background of Related Art

Today, many surgical procedures are performed through small incisions in the skin, as compared to the larger incisions typically required in traditional procedures, in an effort to reduce both trauma to the patient and recovery time. Generally, such procedures are referred to as "endoscopic", unless performed on the patient's abdomen, in which case the procedure is referred to as "laparoscopic". Throughout the present disclosure, the terms endoscopic and laparoscopic may be used interchangeably. Additionally, surgical procedures may be performed though a naturally occurring orifice, e.g., anus or vagina. Collectively, these are surgical procedures are generally referred to as minimally invasive.

In a continuing effort to minimize scarring and reduce recovery time, many laparoscopic procedures are being performed through a single incision. Ports for use in single incision surgery are known, one of which is disclosed in commonly owned U.S. patent application Ser. No. 12/244,024, the contents of which are hereby incorporated by reference in their entirety. The port includes multiple lumen such that a surgeon may simultaneously insert multiple devices through the port and manipulate them within the abdominal cavity.

Although scarring is significantly reduced using the single incision procedures, a visible scar may remain. To eliminate the possibility of visible scarring the abdominal cavity may be accessed through the vagina of a female patient. Rigid tubular ports configured for use in traditional single incision surgery may require a sealing system and/or may include edges that could damage delicate internal organs. Additionally, due to the substantial length required to access the abdominal cavity through the vagina, manipulation and triangulation of surgical devices inserted through these ports may be difficult.

Therefore, it would be beneficial to have a port configured for transvaginally accessing the abdominal cavity.

SUMMARY

Accordingly, an access port for transvaginally accessing the abdominal cavity is provided. The access port includes an elongated member having proximal and distal ends and a central portion therebetween and a retention mechanism formed on the distal end of the elongated member. The retention mechanism includes a first configuration for inserting the distal end of the elongated member within an opening and a second configuration for selectively securing the elongated member within an opening.

In one embodiment, the distal end of the access port is configured to be selectively received through an incision in the posterior fornix of a vagina. The distal end may be configured to be selectively received within an abdominal cavity of a patient. The distal end of the elongated member may include multiple lumens extending therethrough. Each of the multiple lumens may be configured to receive a surgical instrument. The elongated member may be composed of foam, rubber or other elastic material. The retention mechanism may include a selectively inflatable member, a plurality of anchor members or a plurality of fins.

Also provided is a method of performing a surgical procedure. The method includes the steps of providing an access port including a retention mechanism configured to selectively retain the access port within a natural opening of a patient, forming an incision in the wall of the natural opening into a body cavity of the patient, and inserting a distal end of the access port into the natural opening and through the incision. The method may further include the steps of activating the retention mechanism to secure the distal end of the access port within the abdominal cavity of the patient.

In one embodiment, the retention mechanism includes an inflatable member configured to be inflated to secure the access port within the natural opening. In this manner, the method further includes the step of inflating the inflatable member.

In another embodiment, the retention mechanism includes a plurality of anchor members configured to be extended to insert the access port within the natural opening. In this manner, the method further includes the step of extending the plurality of anchor members prior to insertion of the access port into the natural opening and releasing the plurality of anchor members upon reception of the distal end thereof through the incision.

In yet another embodiment, the retention mechanism includes a plurality of radially extending fins configured to secure the access port within the natural opening. In this manner, the method further includes the step of extending the plurality of radially extending fins outward to secure the access port within the natural opening.

BRIEF DESCRIPTION OF THE DRAWINGS

The accompanying drawings, which are incorporated in and constitute a part of this specification, illustrate embodiments of the disclosure and, together with a general description of the disclosure given above, and the detailed description of the embodiment(s) given below, serve to explain the principles of the disclosure, wherein.

DETAILED DESCRIPTION

Figure 1:
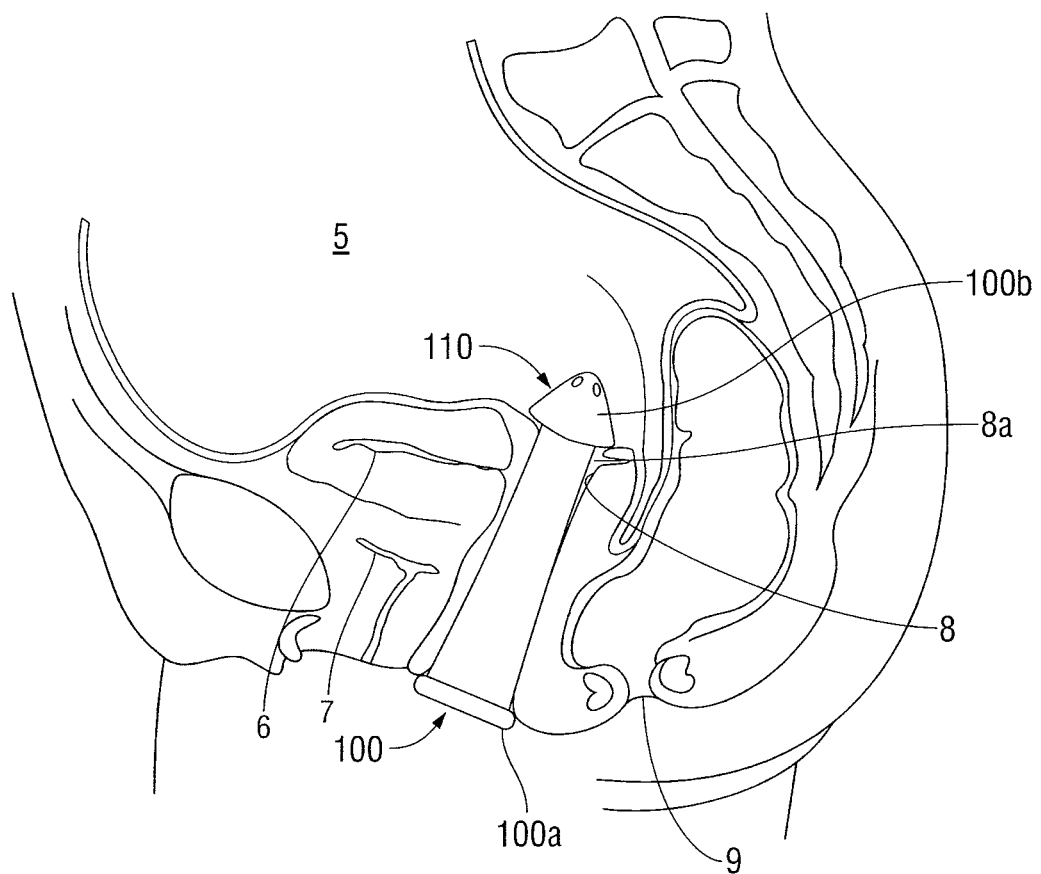
FIG. 1 is an illustration of the internal anatomy of a female patient including an embodiment of an access port according to the present disclosure received transvaginally.

In the drawings and in the description which follows, in which like reference numerals identify similar or identical elements, the term "proximal" will refer to the end of the apparatus which is closest to the clinician during use, while the term "distal" will refer to the end which is farthest from the clinician, as is traditional and known in the art.

With reference to FIG. 1, an illustration of the internal anatomy of a female patient is shown including the abdominal cavity 5, uterus 6, urinary bladder 7, vagina 8 and anus 9. A distal end 100b of an embodiment of the present disclosure, shown generally as access port 100, is received through an incision 8a formed in the posterior fornix of vagina 8 while a proximal end 100a of access port 100 remains accessible by a surgeon. A retention mechanism 110 formed on distal end 100b maintains access port 100 within vagina 8.

Figure 2:
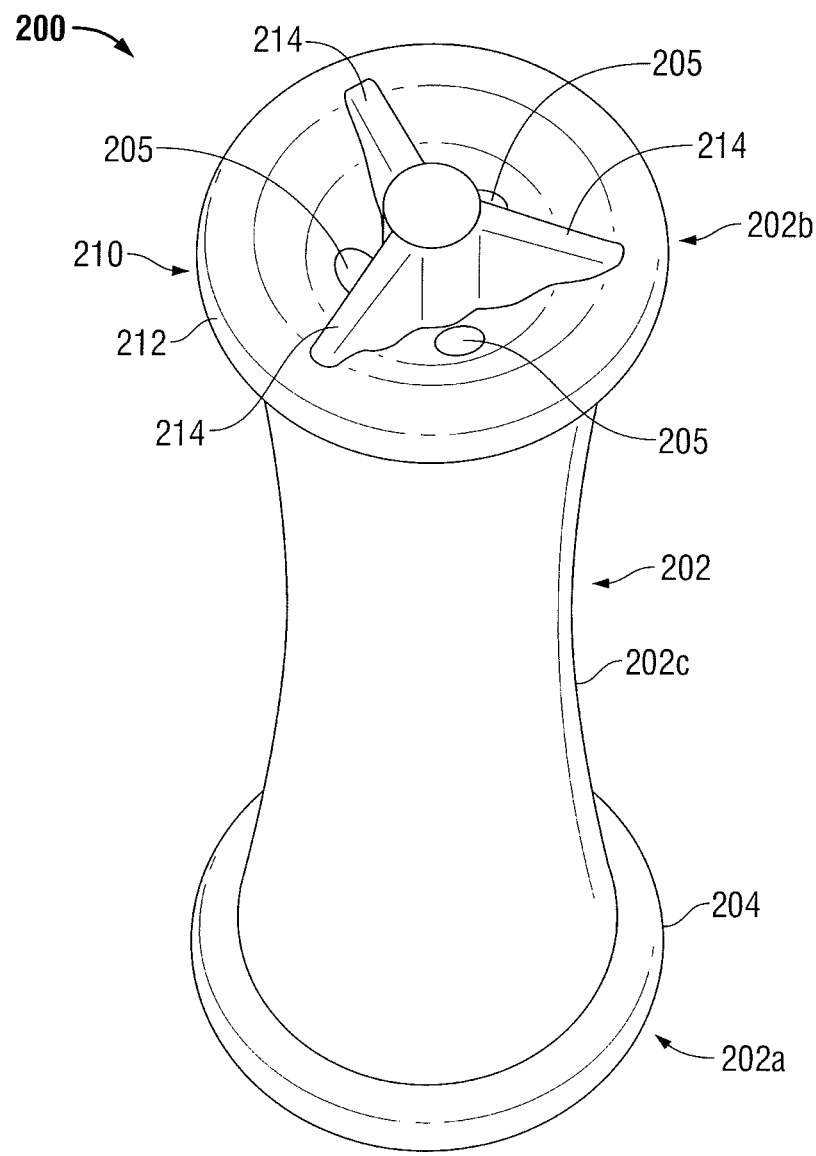
FIG. 2 is a perspective view of an access port according to another embodiment of the present disclosure.
Figure 3:
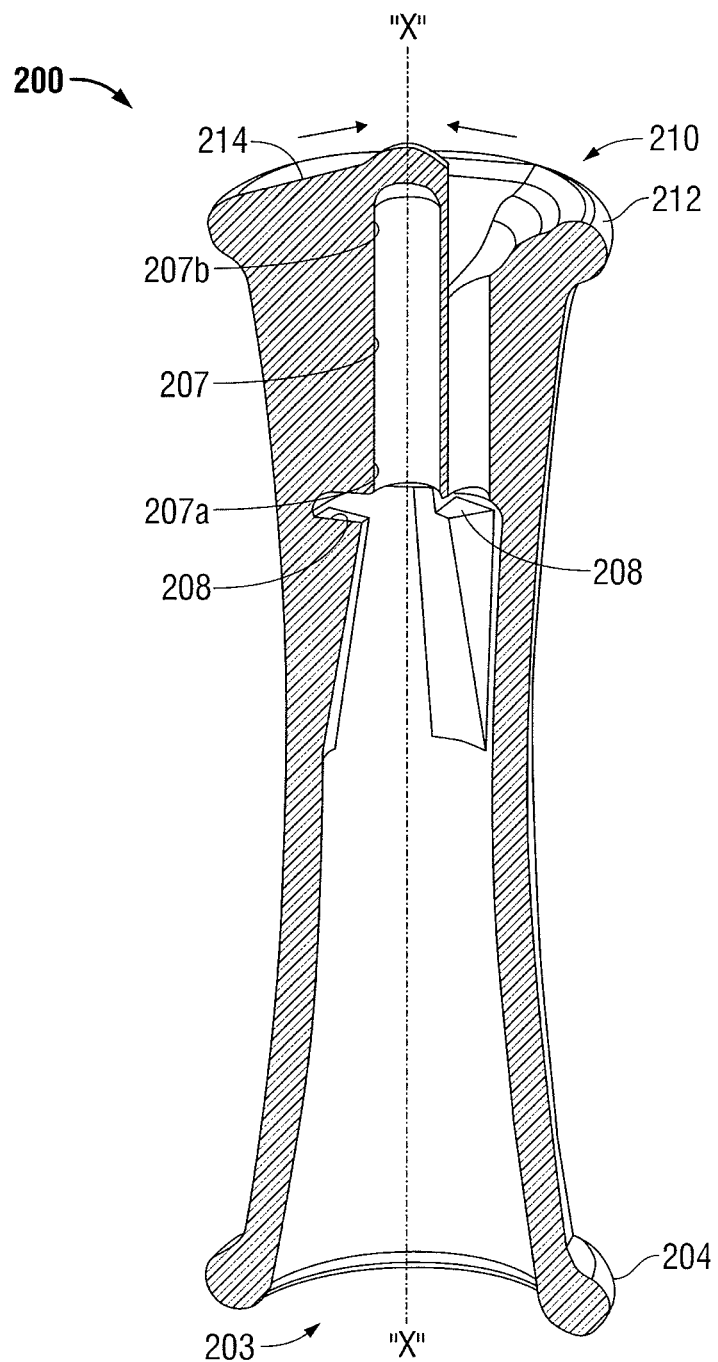
FIG. 3 is a cross-sectional side view of the access port of FIG. 2.

Turning now to FIGS. 2 and 3, an embodiment of the present disclosure is shown generally as access port 200. Although, as shown and as will be discussed, access port 200 is configured to provide a surgeon transvaginal access to abdominal cavity 5 (FIG. 1), access port 200 may be configured for use through other naturally occurring orifices, e.g., anus, or in a more conventional manner, for accessing the abdominal cavity through the abdominal wall.

Access port 200 includes an elongated member 202 having a substantially hourglass shape when viewed from the side. Access port 200 is composed of foam or other elastic and/or pliable material. Although intended to be disposable, access port 200 may composed of a material and/or include a coating such that it may be sterilized and reused.

Still referring to FIGS. 2 and 3, elongated member 202 includes a substantially open proximal end 202a, a substantially closed distal end 202b and a central portion 202c therebetween. Proximal end 202a of elongated member 202 defines a proximal lumen 203 configured to provide a surgeon with a passage for accessing abdominal cavity 5 (FIG. 1) with one or more endoscopic instruments. A rim 204 is formed on proximal end 202a of elongated member 202 and is configured to prevent over-insertion of access port 200 within vagina 8 (FIG. 1). In one embodiment, when access port 200 is operably received within vagina 8, rim 204 is maintained external of vagina 8. As will be discussed in further detail below, the length and diameter of access port 200 may be varied depending on the dimensions of vagina 8 and/or the procedure being performed through access port 200. Access port 200 may include a coating or cover (not shown) for facilitating insertion of access port 200 into and through vagina 8.

Distal end 202b of elongated member 202 defines a plurality of distal lumens 205. Although shown including three distal lumens 205, it is envisioned that access port 200 may include one or more distal lumens 205. In one embodiment, and as shown, distal lumens 205 are each parallel to a central axis "X". In alternate embodiments, one or more of lumens 205 may be angled towards or away from central axis "X" and/or towards or away from each other. Distal lumens 205 may have the same diameter, as shown, or instead may include diameters of various lengths. Distal lumens 205 are sized to receive instruments in a sealing manner. Alternatively, or in addition, one or all of distal lumens 205 may include a seal member or mechanism for sealing respective distal lumen 205.

With reference still to FIGS. 2 and 3, distal end 202b of access port 200 includes a retention mechanism 210. Retention mechanism 210 includes a flange 212 configured to securely maintain distal end 202b of access port 200 within abdominal cavity 5 through incision 8a formed in the posterior fornix of vagina 8 (FIG. 1). Flange 212 is supported by ribs 214 extending radially inward from flange 212. Flange 212 is configured to collapse radially during insertion into vagina 8 to ease the insertion. Flange 212, in combination with rim 204, operate to secure access port 200 within vagina 8 and minimize longitudinal movement of access port 200 as a procedure is being performed therethrough. Central portion 202c of elongated member 202 is configured to extend the length of vagina 8 such that distal end 202b of elongated member 202, including flange 212, are received within abdominal cavity 5 while proximal end 202a of elongated member 202, including rim 204, is maintained external to vagina 8.

Figure 4:
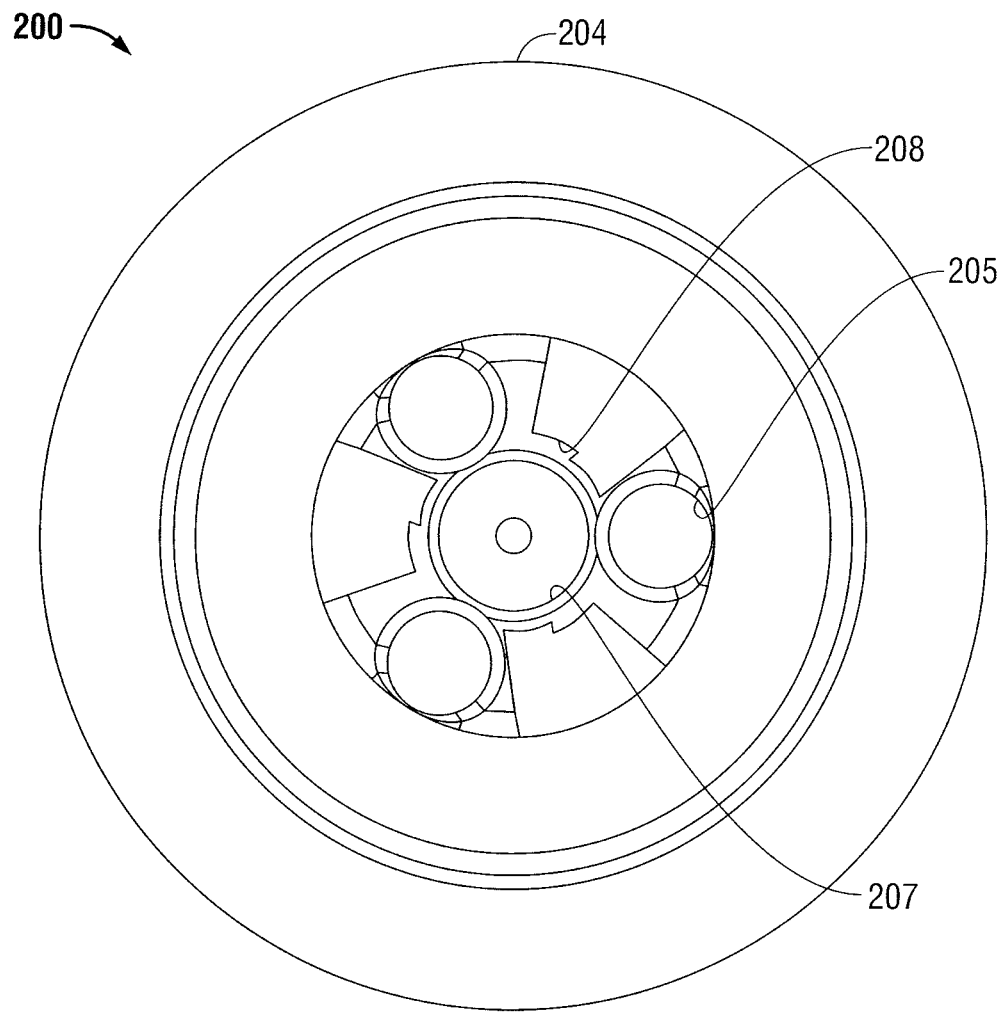
FIG. 4 is a proximal end view of the access port of FIGS. 2 and 3.

With reference now to FIGS. 3 and 4, distal end 202b of elongated member 202 further includes a blind lumen 207. Blind lumen 207 includes an open proximal end 207a and a closed distal end 207b. Blind lumen 207 is configured to selectively receive a distal end of an insertion instrument (not shown). Blind lumen 207 may include grooves or recesses (not shown) configured to receive tabs or protrusions (not shown) formed on the insertion instrument such that access port 200 may be more securely engaged by the insertion instrument.

With reference still to FIGS. 3 and 4, notches 208 are formed in central portion 202c of elongated member 202 about proximal lumen 203. Notches 208 are configured to selectively engage tabs (not shown) formed on a removal instrument (not shown) for assisting in removal of access port 200.

With reference now to FIGS. 1-4, in use, incision 8a is first formed in the posterior fornix of vagina 8 to access abdominal cavity 5. A distal end of an insertion instrument (not shown) is then inserted within blind lumen 207 formed in distal end 202b of elongated member 202. Distal end 202b of access port 200 is then inserted into vagina 8 and through incision 8a such that flange 212 is received within abdominal cavity 5. In one procedure, the size of access port 200 is such that rim 204 is maintained external of vagina 8. As discussed above, access port 200 may include a coating (not shown) for facilitating insertion thereof. Alternatively, a lubricant may be applied to access port 200 to facilitate insertion.

Still referring to FIGS. 1-4, once properly positioned within vagina 8, the distal end of the insertion instrument (not shown) is removed from blind lumen 207 and access port 200 is ready for use. One or more endoscopic instruments may be inserted through distal lumen 205 of access port 200 to complete a surgical procedure. A source of insufflation gas may be connected to one of distal lumen 205 for insufflating abdominal cavity 5.

With reference still to FIGS. 1-4, upon completion of a procedure, endoscopic instruments and/or insufflation supply line (not shown) are removed from access port 200. A distal end of a removal instrument (not shown) is then received within proximal lumen 203. Tabs (not shown) formed on the distal end of the removal instrument engage notches 208 formed in central portion 202c of elongated member 202. Once securely engaged with access port 200, the removal instrument is used by the surgeon to pull access port 200 from within vagina 8. Incision 8a is closed in a conventional manner.

Figure 5:
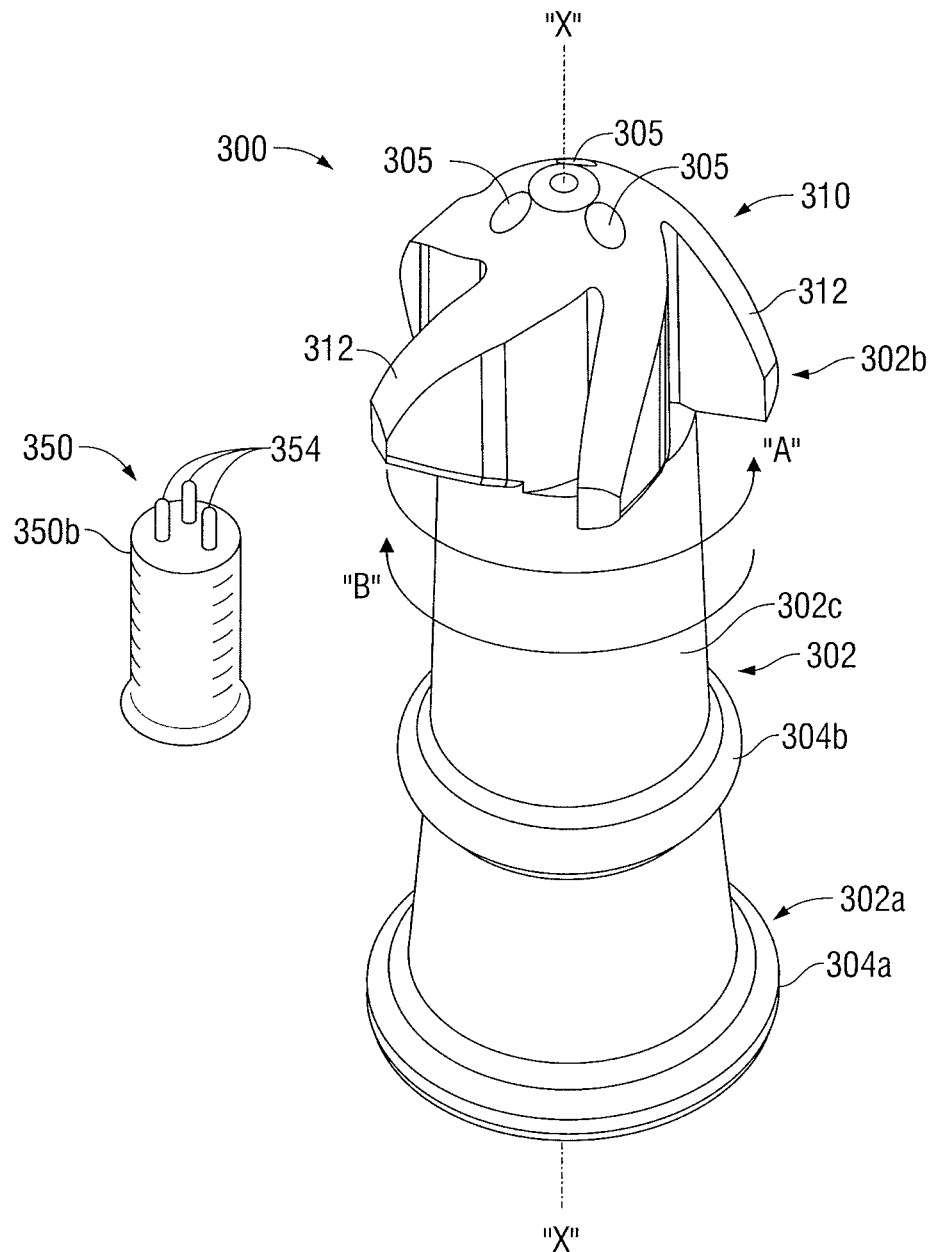
FIG. 5 is a perspective side view of an access port according to yet another embodiment of the present disclosure, in a collapsed position and including an insertion instrument.
Figure 6:
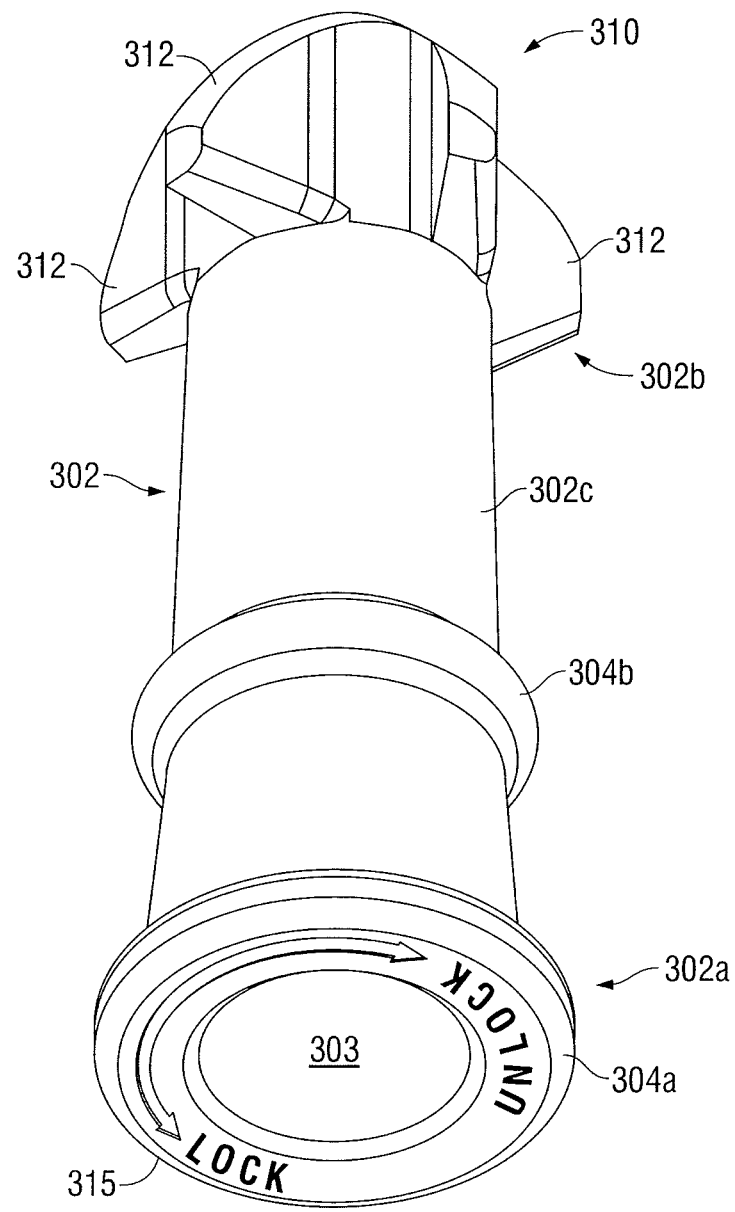
FIG. 6 is a perspective end view of the access port of FIG. 5.

With reference now to FIGS. 5 and 6, an alternate embodiment of an access port configured for transvaginal use is shown generally as access port 300. Access port 300 is substantially similar to access port 200 described hereinabove, and therefore will only be described as relates to the differences therebetween. Access port 300 includes an elongated member 302 including proximal and distal ends 302a, 302b, respectively, and a central portion 302c therebetween. Access port 300 includes three distal lumens 305 formed in distal end 302b of elongated member 302. It is envisioned that access port 300 may include one or more distal lumens 305. In one embodiment, proximal end 302a of elongated member 302 is tapered and includes a first and a second rim 304a, 304b. First and second rims 304a, 304b are configured to prevent over-insertion of access port 300 within vagina 8. Rims 304a, 304b may also be configured to facilitate removal of access port 300 from within vagina 8.

With reference still to FIGS. 5 and 6, distal end 302a of elongated member 302 includes a retention mechanism 310. Retention mechanism 310 includes a plurality of radially extendable fins 312. Fins 312 are configured to selectively retain access port 300 within vagina 8 (FIG. 1). Rotation of access port 300 about a longitudinal axis "X" in a first direction, as indicated by arrow "A" (counter-clockwise as shown in FIGS. 5 and 6), during insertion into vagina 8 causes fins 312 to collapse inwardly, thereby reducing the circumference of distal end 302b and easing insertion of access port 300 into vagina 8 and through incision 8a (FIG. 1). Once distal end 302b of elongated member 302 is received within abdominal cavity 5 through incision 8a rotation of access port 300 about longitudinal axis "X" in a second direction, as indicated by arrow "B" (clockwise as shown in FIGS. 5 and 6), causes fins 312 to expand, thereby increasing the circumference of distal end 302b and securing access port 300 within incision 8a. Frictional engagement of fins 312 with a wall of vagina 8 permits fins 312 to collapse or expand, as indicated above, upon rotation of access port 300. It is envisioned that access port 300 may include a mechanism for securing fins 312 in the collapsed and/or expanded conditions to prevent accidental collapsing and/or expanding of fins 312.

With reference to FIG. 6, in one embodiment, indicia 315 located on proximal end 302a of elongated body 302 indicates to a surgeon in which direction to rotate elongated member 302 to engage, e.g., lock, (by expanding fins 312) or disengage, e.g., unlock, (by collapsing fins 312) retention mechanism 310 of access port 300.

With reference back to FIG. 5, one embodiment of an insertion instrument configured for insertion of access port 300 is shown generally as insertion instrument 350. A distal end 350b of insertion instrument 350 is configured to be received within proximal lumen 303 of access port 300. Distal end 350b includes a plurality of protrusions 354 extending distally therefrom configured to engage distal lumens 305 formed in distal end 302b of elongated member 302. A proximal end 350a of insertion instrument 350 is configured to facilitate grasping by a surgeon such that insertion instrument 350 may be used to rotate access port 300.

In use, incision 8a is formed and access port 300 is inserted within vagina 8. Insertion of access port 300 may be completed with or without the use of insertion instrument 350. A lubricant (not shown) may be applied to elongated member 302 to facilitate insertion of access port 300. As discussed above, as elongated member 302 is received with vagina 8, elongated member 302 is rotated in a first direction, as indicated by arrows "A", to reduce the circumference of distal end 302b and ease insertion thereof through vagina 8 and incision 8a. Once distal end 302b is received through incision 8a, elongated member 302 is rotated in a second direction, as indicated by arrows "B", to expand fins 312 and secure access port 300 within vagina 8 and through incision 8a.

Once properly positioned within vagina 8, multiple instruments may be insert through access port 300 to complete a procedure. Once the procedure is complete, access port 300 is removed by rotating elongated member 302 in the first direction, as indicated by arrow "A", as proximal end 302a of elongated member 302 is grasped by a surgeon, either using his/her hand or a removal instrument (not shown), and is pulled from vagina 8. As discussed above, rotation of elongated member 302 causes fins 312 to collapse, thereby reducing the circumference of distal end 302b and aiding in withdrawal thereof through incision 8a and vagina 8.

Figure 7:
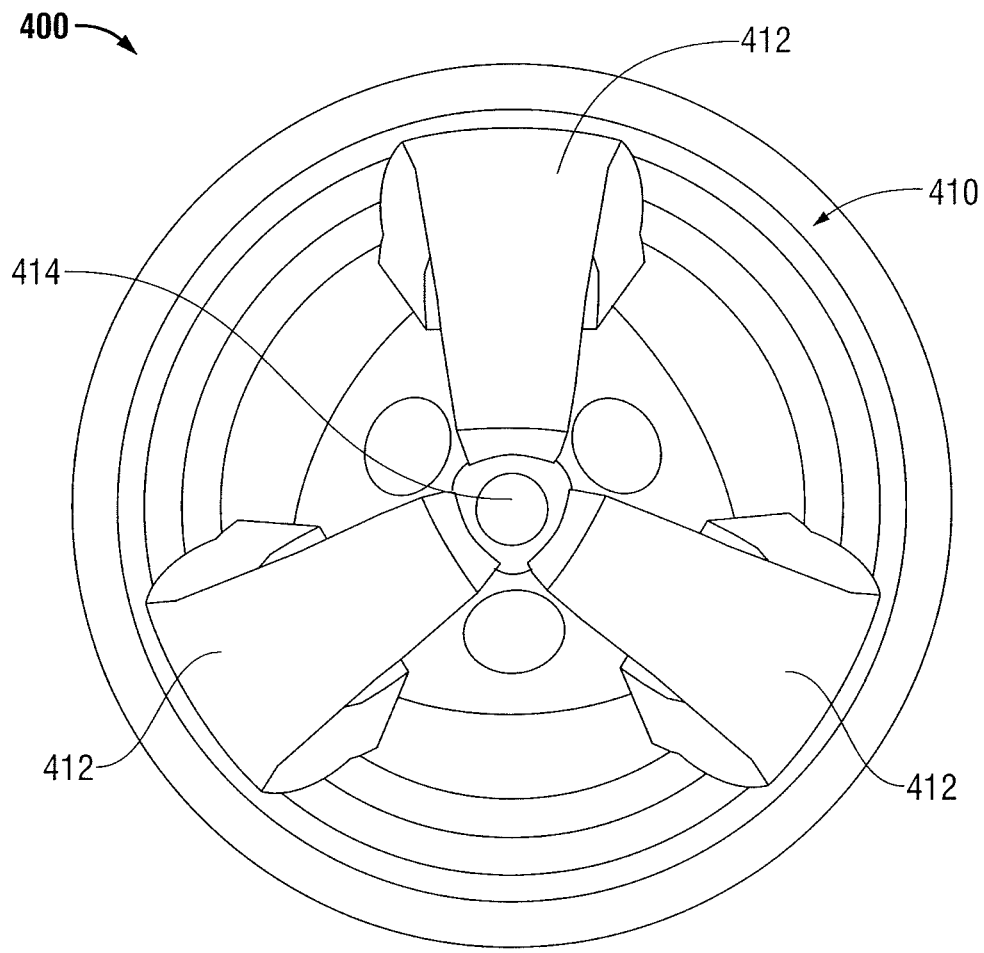
FIG. 7 is a distal end view of an access port according still another embodiment of the present disclosure, in a first or relaxed condition.
Figure 8:
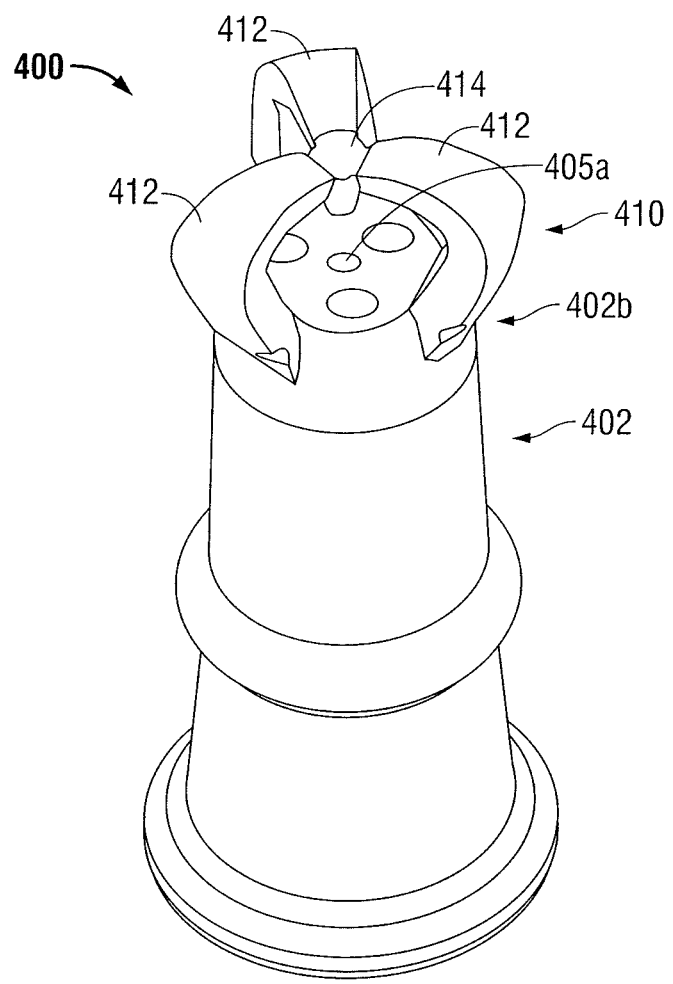
FIG. 8 is a perspective side view of the access port of FIG. 7 in the first or relaxed condition.
Figure 9:
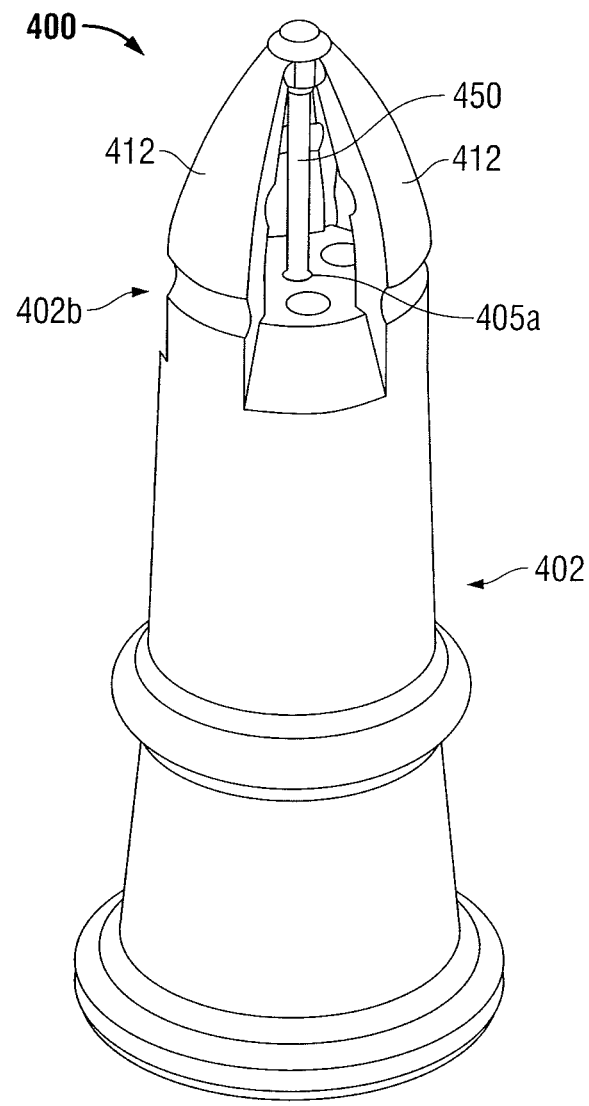
FIG. 9 is a perspective side view of the access port of FIGS. 6 and 7, in a second or straightened condition.

Turning now to FIGS. 7-9, another embodiment of an access port according to the present disclosure is shown generally as access port 400. As with access ports 200 and 300, access port 400 is substantially similar thereto and will be described only as relates to the differences therebetween. Access port 400 includes a retention mechanism 410 formed on a distal end 402b of an elongated member 402. Retention mechanism 410 includes a plurality of anchor members 412 operably connected to one another at a distal tip 414. Although shown with three anchor members 412, it is envisioned that access port 400 may include two or more anchor members 412. In a first or relaxed condition (FIG. 8) anchors 412 bow radially outward to enlarge distal end 402b. When in the relaxed condition, enlarged distal end 402b is configured to secure access port 400 within vagina 8. In a second or straightened condition (FIG. 9), anchor members 412 are elongated or straightened to narrow distal end 402b. Narrowing of distal end 402b facilitates insertion of elongated member 402 within vagina 8 and through incision 8a.

With continued reference to FIGS. 7-9, in one embodiment, an insertion rod 450 (FIG. 9) extending from an insertion instrument (not shown) is inserted into a distal lumen 405a formed in distal end 402b of elongated member 402 is used to straighten anchor members 412. Once insertion rod 450 is removed from distal lumen 405a, anchor members 412 flex outwardly and return to the first or relaxed condition. In this manner, distal end 402b of elongated member 402 is configured to be inserted through and removed from vagina 8 and incision 8a when in a second or straightened condition and is configured to be secured within vagina 8 and through incision 8a when in a first or relaxed condition.

It is envisioned that access port 400 may include a straightening mechanism (not shown) for straightening and releasing anchor members 412 without the assistance of an insertion instrument. The straightening mechanism may be activated through rotational and/or longitudinal manipulation of access assembly 400 by a user.

Figure 10:
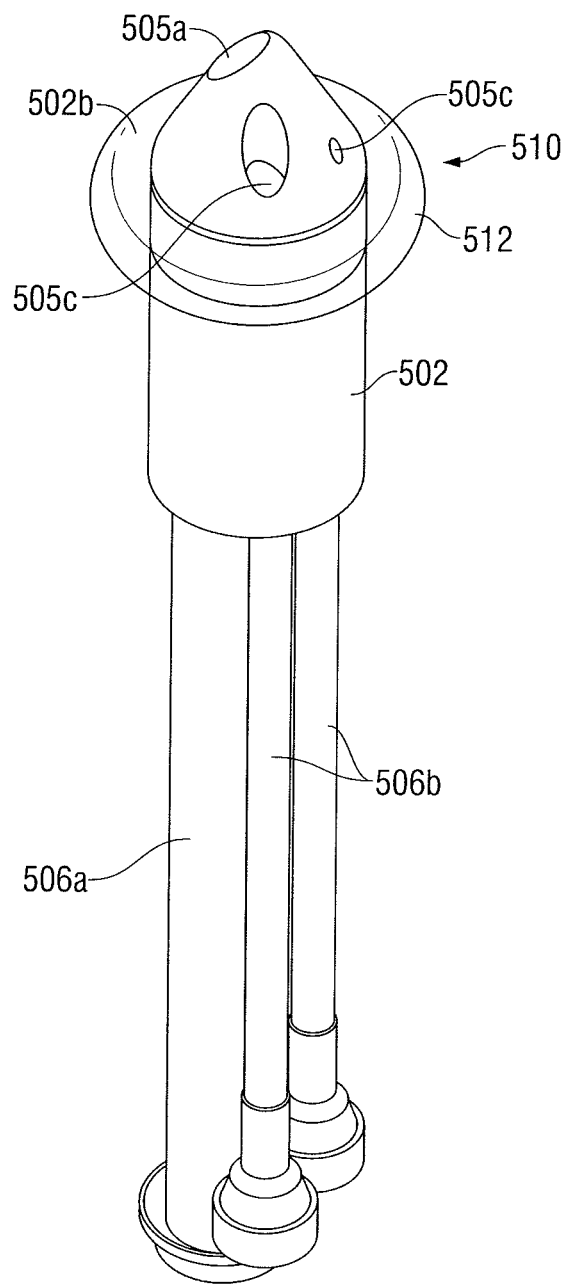
FIG. 10 is a side view of an access port according to still yet another embodiment of the present disclosure.
Figure 11:
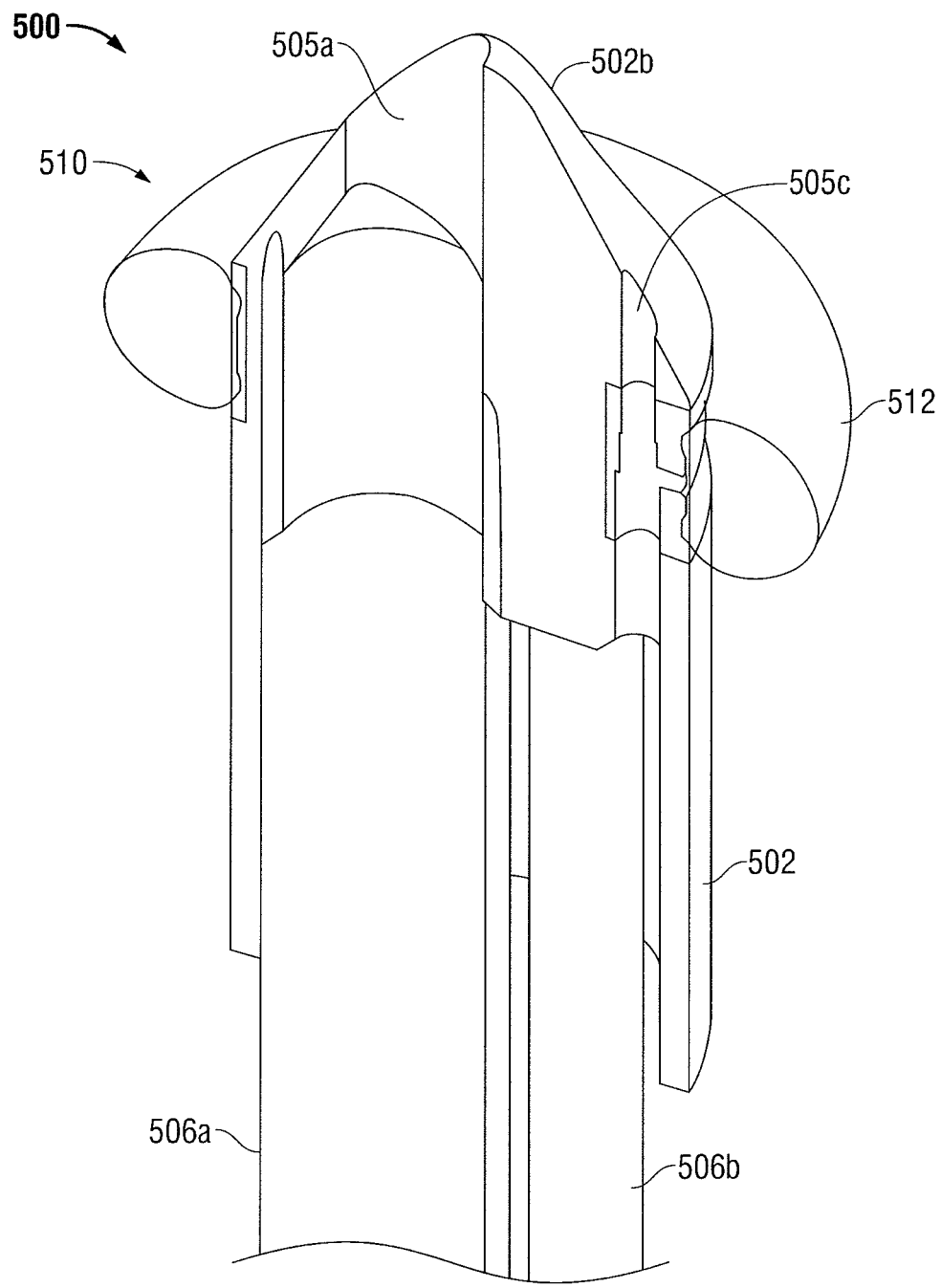
FIG. 11 is an enlarged cut-away view of the distal end of the access port of FIG. 10.
Figure 12:
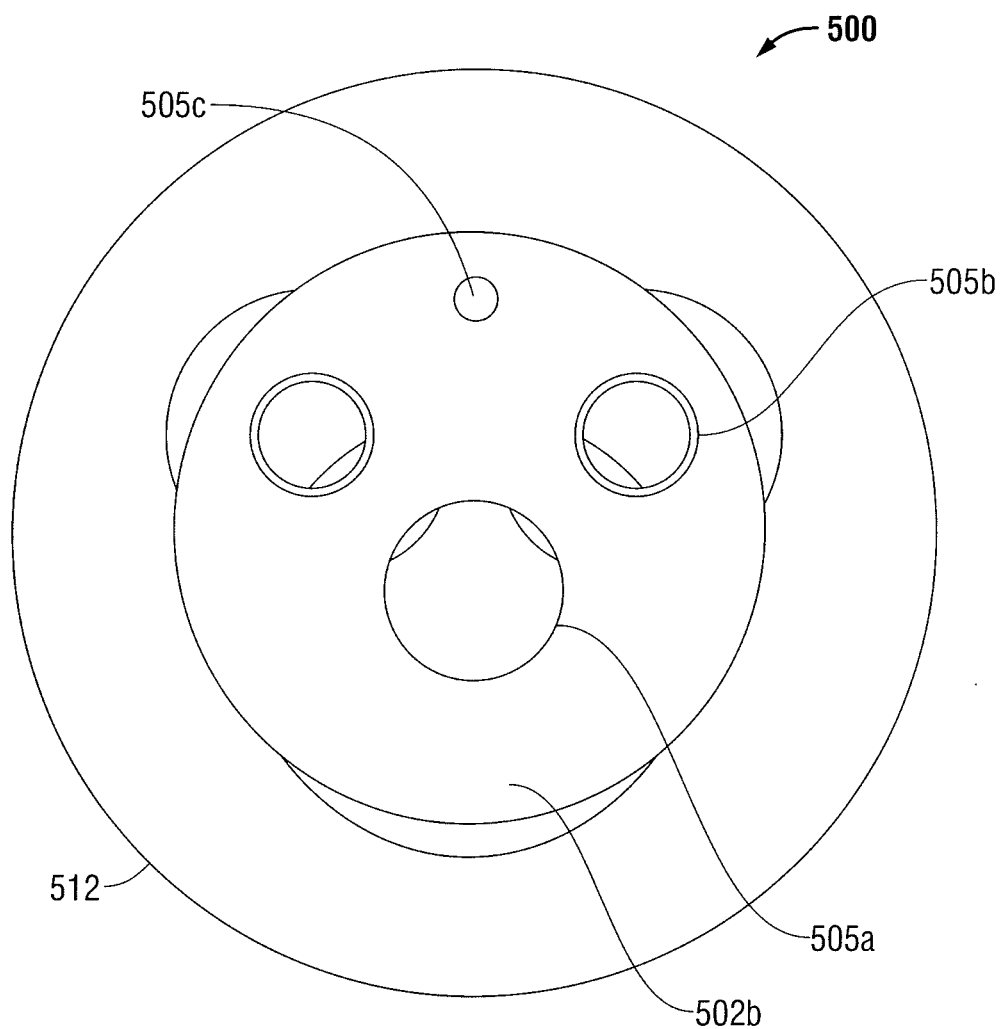
FIG. 12 is a distal end view of the access port of FIGS. 10 and 11.

With reference now to FIGS. 10-12, yet another embodiment of an access port according to the present disclosure is shown generally as access port 500. Access port 500 includes a substantially cylindrical member 502 having a conical distal end 502b. A plurality of distal lumens 505a, 505b, 505c extend through cylindrical member 502. Cannulas 506a, 506b extend distally from and are operably connected to distal lumen 505a, 505b, respectively. As shown, cannula 506a and distal lumen 505a form a centrally located opening that permits visualization therethough. Cannula 506a and distal lumen 505a may also be configured to receive a cutting instrument for forming incision 8a (FIG. 1). Distal lumen 505c defines an insufflation channel configured to direct insufflation gas into abdominal cavity 5 (FIG. 1). As will be discussed in further detail below, distal lumen 505c may also be connected with an inflatable member 512 to provide gas for inflating an inflatable member 512. Cannulas 506b and distal lumens 505b are configured to receive endoscopic instruments (not shown) therethrough.

With reference still to FIGS. 10-12, distal end 502b of cylindrical member 502 includes a retention mechanism 510. Retention mechanism 510 includes inflatable member 512 extending about distal end 502b of cylindrical member 502. Inflatable member 512 is configured to be inflated once distal end 502b of cylindrical member 502 is received through incision 8a. Inflatable member 512 operates to secure cylindrical member 502 within vagina 8. Gas is provided to inflatable member 512 remotely through distal lumen 505c. In an alternative embodiment, gas may be provided to inflate inflatable member 512 from a gas source (not shown) located within cylindrical member 502.

Figure 13:
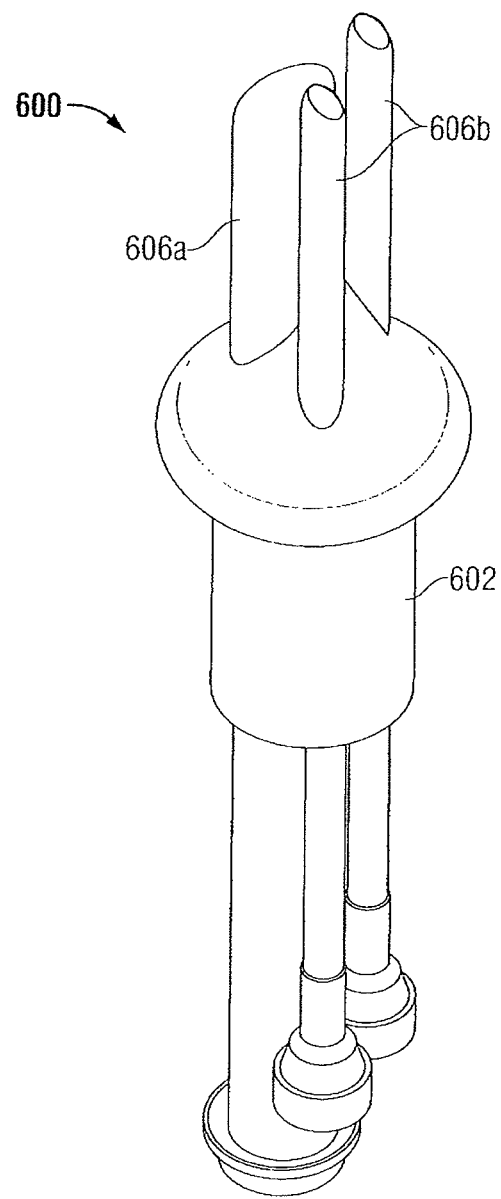
FIG. 13 is an access port according to yet another embodiment of the present disclosure.

Turning to FIG. 13, in still yet another embodiment of an access port according to the present disclosure and shown generally as access port 600, cannulas 606a, 606b are slideably connected to cylindrical body 602 such that each may be selectively extended therethrough.

With reference now to FIGS. 14-17, another embodiment of the an access port according to the present disclosure is shown generally as access port 700. Access port 700 incorporates features of the access ports described hereinabove. Access port 700 includes an elongated member 702 including proximal and distal ends 702a, 702b, respectively, and a central portion 702c therebetween. Access port 700 includes one or more lumens 705 formed in distal end 702b of elongated member 702. It is envisioned that access port 700 may include one, two, three (FIG. 16), four (FIG. 17), or more distal lumens 705. Access port 700 may also include an integrated seal (not shown) formed over a distal end of distal lumen 705. The integrated seal forms a cover or skin over the distal end of distal lumen 705 which are pierced during insertion of a cannula or other instrument. Alternatively, distal lumen 705 may be sealed during insertion using an introducer (FIG. 18) having detachable 'prongs' (not shown) which are configured for plugging distal lumen 705. In another embodiment, distal end 702 of access port 700 may include a condom-like cover (not shown) that gets pierced during cannula insertion.

Figure 15:
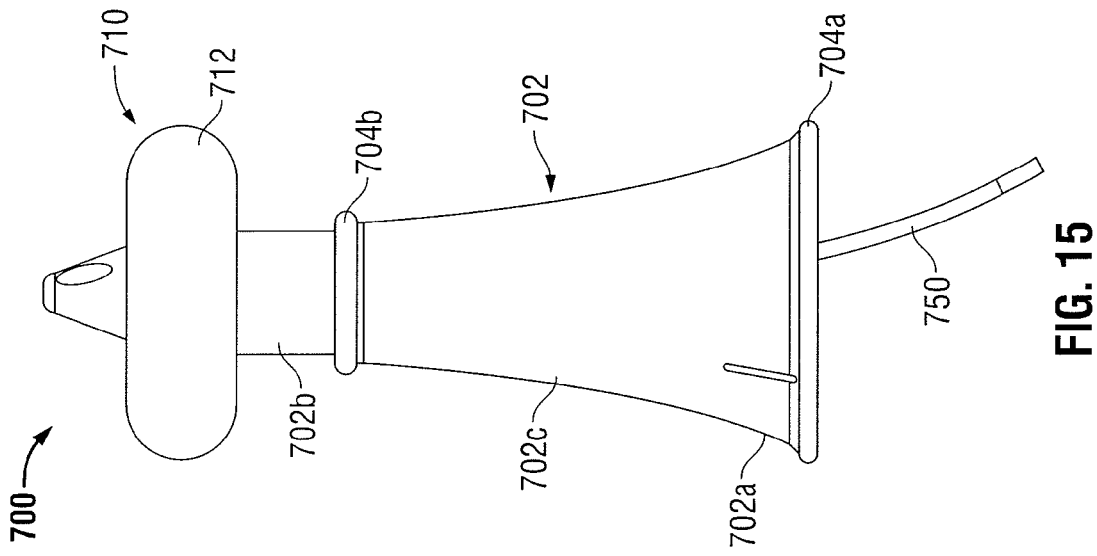
FIG. 15 is a side view of the access port of FIG. 14, wherein the inflatable member is inflated.
Figure 14:
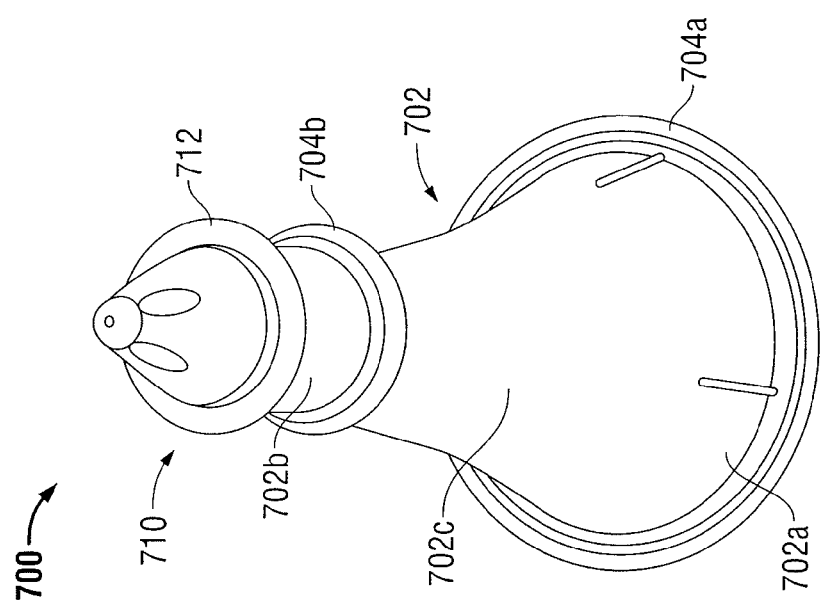
FIG. 14 is a perspective view of an access port according another embodiment of the present disclosure having an inflatable member in a deflated condition.
Figure 16:
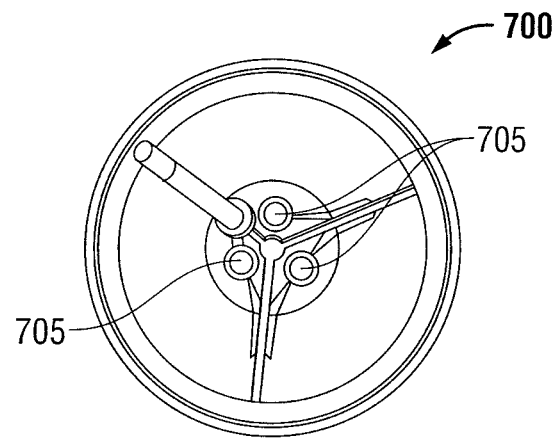
FIG. 16 is a proximal end view of the access port of FIGS. 14 and 15 including three lumens.
Figure 17:
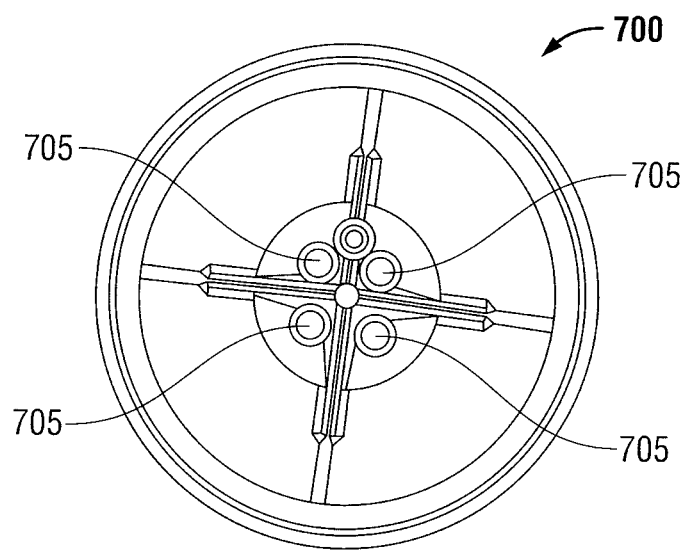
FIG. 17 is a proximal end view of the access port of FIGS. 14 and 15 including four lumens.

With reference to FIGS. 14 and 15, as shown, proximal end 702a of elongated member 702 is tapered and includes first and second rims 704a, 704b. First and second rims 704a, 704b are configured to prevent over-insertion of access port 700 within vagina 8. Rims 704a, 704b may also be configured to facilitate removal of access port 700 from within vagina 8.

With references still to FIGS. 14 and 15, distal end 702b of elongated member 702 includes a retention mechanism 710. Retention mechanism 710 includes inflatable member 712 extending about distal end 702b of elongated member 702. Inflatable member 712 is configured to be inflated (FIG. 15) once distal end 702b of elongated member 702 is received through incision 8a. Inflatable member 712 operates to secure elongated member 702 within vagina 8. Gas is provided to inflatable member 712 remotely through inflation tube 750. In an alternative embodiment, gas may be provided to inflate inflatable member 712 from a gas source (not shown) located within elongated member 702. In one embodiment, inflatable member 712 includes a valve or other safety mechanism (not shown) configured to prevent over-inflation of inflatable member 712. Alternatively, access port 700 may be provided with a syringe (not shown) having a set volume for controlled inflation of inflatable member 712.

Figure 18:
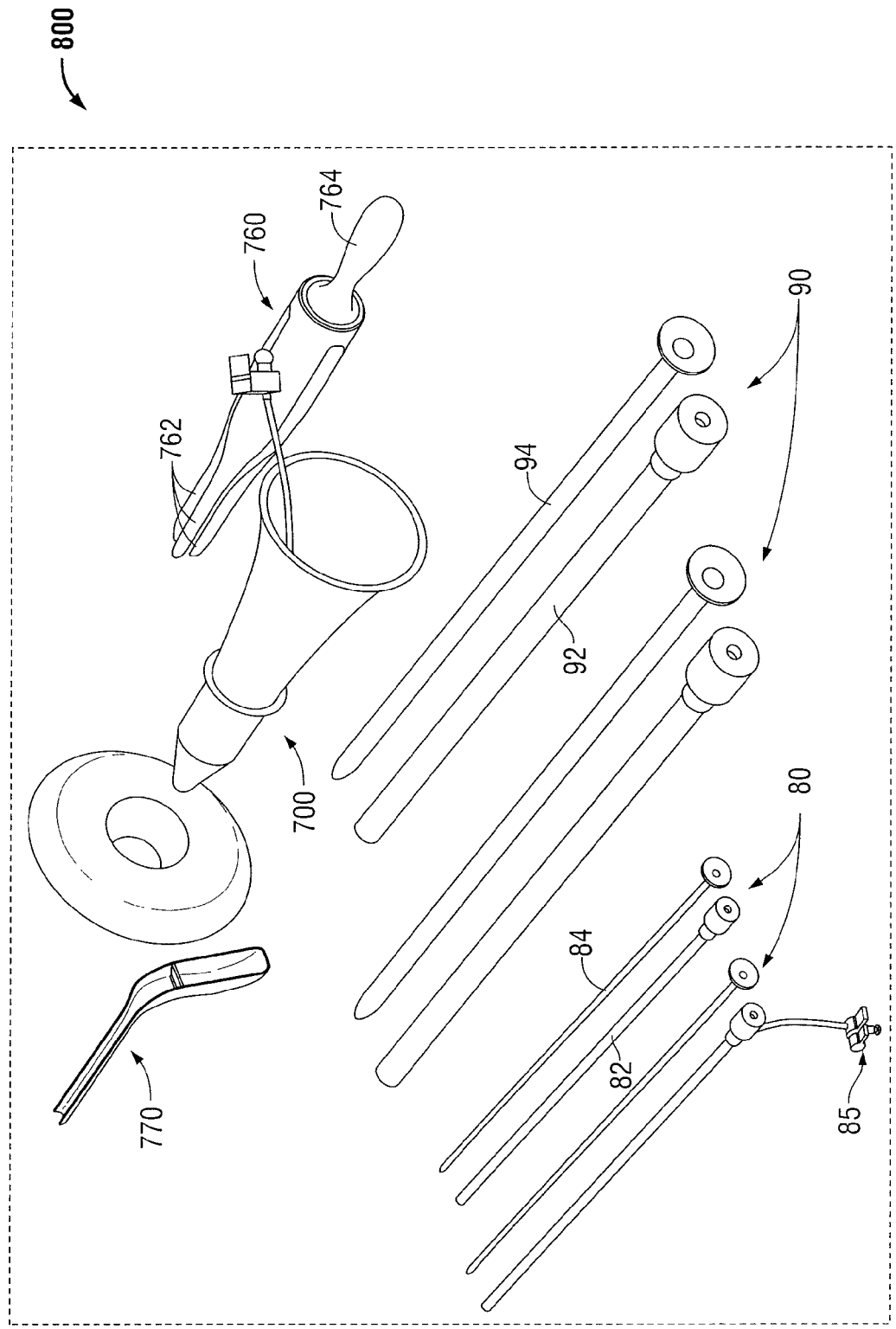
FIG. 18 is a perspective view of the access port of FIG. 14 included in a kit for transvaginal surgery.

Turning now to FIG. 18, a kit for use in transvaginal surgery is shown generally as kit 800. As shown, kit 800 includes an access port 700, an introducer 760 and an inserter 770, each configured for facilitating insertion of access port 700, one or more sets of small cannula/obturator assemblies 80 and one or more sets of large cannula/obturator assemblies 90. As shown, kit 800 includes access port 700, however, it is envisioned that kit 800 may include any of the above-described access ports.

With continued reference to FIG. 18, introducer 760 includes a plurality of prongs 762 configured to be received within distal lumen 705 and a handle 764 configured to facilitate engagement by a user. The number of prongs 762 correspond with the number of distal lumen 705 defined by access port 700. As shown, introducer 760 includes four prongs 762. Inserter 770 defines a substantially shoe-horn shaped member configured to spread an incision during insertion of access port 700 through the incision. Inserter 770 may be made of plastic, metal or other suitable material and may include a one-piece moldable design.

Still referring to FIG. 18, kit 800 may include one or more cannula/obturator assemblies 80, 90. Each of cannula/obturator assemblies 80, 90 include a cannula 82, 92 and an obturator 84, 94, respectively. Cannula/obturator assemblies 80, 90 may be of the same or different configurations. As shown, cannula/obturator assemblies 80, 90 may include an insufflation valve 85.

Although specific features of the access ports are shown in some of the drawings and not in others, this is for convenience only as each feature may be combined with any or all of the other features in accordance with the aspects of the present disclosure. Other embodiments will occur to those skilled in the art and are within the scope of the present disclosure.

What is claimed is:
1. An access port for use during transvaginal surgery comprising:
   an elongated flexible member including:
      a conical body portion forming a proximal-most end of the elongated flexible member;
      a cylindrical distal portion extending distally from the conical body portion and defining at least one longitudinally extending lumen therein; and
      an atraumatic distal tip portion having a conical shape and extending distally from the cylindrical distal portion, the atraumatic distal tip portion including at least one distal opening of the at least one lumen; and
   a retention mechanism received about the elongated flexible member between the cylindrical distal portion and the atraumatic distal tip portion, the retention mechanism including a first configuration for inserting a distal end of the elongated flexible member within an opening and a second configuration for selectively securing the elongated flexible member within the opening.

2. The access port of claim 1, wherein the cylindrical distal portion is configured to be selectively received through an incision in the posterior fornix of a vagina.

3. The access port of claim 1, wherein the cylindrical distal portion is configured to be selectively received within an abdominal cavity of a patient.

4. The access port of claim 1, wherein the cylindrical distal portion of the elongated flexible member includes multiple lumens extending therethrough.

5. The access port of claim 4, wherein each of the multiple lumens is configured to receive a surgical instrument.

6. The access port of claim 4, wherein each of the multiple lumens is configured to receive a surgical instrument in a sealing manner.

7. The access port of claim 1, wherein the elongated flexible member is composed of foam.

8. The access port of claim 1, wherein the elongated flexible member is composed of rubber.

9. The access port of claim 1, wherein the retention mechanism includes a selectively inflatable member.

10. The access port of claim 1, wherein at least one of a proximal end and a distal end of the conical body portion includes a rim.

11. The access port of claim 1, including a rim formed between the cylindrical distal portion and the conical body portion.

12. The access port of claim 1, wherein the atraumatic distal tip portion is frustoconical.

13. The access port of claim 12, wherein the at least one distal opening is formed in a sidewall of the frustoconical atraumatic distal tip portion.

14. The access port of claim 1, wherein the conical body portion, the cylindrical distal portion, and the atraumatic distal tip portion of the elongated flexible member are integrally formed.

* * * * *